United States Patent [19]
Lihl et al.

[11] Patent Number: 6,041,686
[45] Date of Patent: Mar. 28, 2000

[54] MICROTOME HAVING AN OSCILLATING BLADE

[75] Inventors: Reinhardt Lihl; Anton Lang, both of Vienna, Austria

[73] Assignee: Leica Mikrosysteme Aktiengesellschaft, Vienna, Austria

[21] Appl. No.: 08/961,253

[22] Filed: Oct. 30, 1997

[30] Foreign Application Priority Data

Nov. 1, 1996 [DE] Germany .................. 196 45 107

[51] Int. Cl.[7] ........................................... B26D 5/16
[52] U.S. Cl. ................. 83/628; 83/646; 83/647; 83/697; 83/776; 83/915.5; 74/570
[58] Field of Search ................. 83/628, 646, 647, 83/697, 776, 915.5, 170, 171, 632; 74/49, 570

[56] References Cited

U.S. PATENT DOCUMENTS

| | | | |
|---|---|---|---|
| 4,065,977 | 1/1978 | Buzzi et al. | 74/49 |
| 4,078,439 | 3/1978 | Iturriaga-Notario | 74/53 |
| 4,761,988 | 8/1988 | Kato | 72/452 |
| 4,779,472 | 10/1988 | Brackett | 74/50 |
| 4,905,558 | 3/1990 | Corcoran | 83/862 |
| 5,078,386 | 1/1992 | Hou et al. | 272/31 R |
| 5,336,133 | 8/1994 | Chen | 472/6 |

FOREIGN PATENT DOCUMENTS 1 267 873   5/1968   Germany .

OTHER PUBLICATIONS

"Tissue Sectioning Without Embedding or Freezing", *Vibratome Sectioning Products,* der Firma Ted Pella Inc., pp. 1–4, (1992).

*Primary Examiner*—Peter Vo
*Assistant Examiner*—Kevin G. Vereene
*Attorney, Agent, or Firm*—Foley & Lardner

[57] ABSTRACT

The invention relates to a microtome having a blade oscillating transverse to the direction of advancing the cut, for sections on soft tissue samples. The oscillation frequency of the blade is controlled variably by the rotational speed of an electric motor. At the same time, the oscillation amplitude of the blade is also adjustable variably with the aid of an adjustable eccentric or a displacement device. This makes individual adjustment to the consistency of the tissue sample possible, which leads to improved quality of the microtome sections, in particular to a reduction in the waviness of the sections. This makes significantly thinner microtome sections possible, with corresponding advantages during microscopy.

10 Claims, 3 Drawing Sheets

MICROTOME HAVING AN OSCILLATING BLADE

FIELD OF THE INVENTION

The invention relates to a microtome having an oscillating blade. The invention relates more particularly to a microtome having a blade oscillating transverse to a direction in which the cut advances.

BACKGROUND OF THE INVENTION

Microtomes are employed for cutting samples, in particular biological tissue samples. For this purpose, a thin slice is drawn off from the tissue sample using a blade similar to a razor blade. The tissue sections thereby produced have a thickness which, depending on the sample consistency, lies in a range from micrometers to a few tenths of a micrometer. Thin tissue sections of this type may be observed and examined in a microscope in transmitted light. The layer thicknesses of the tissue sections must be dimensioned such that they have an adequate transmission of the illuminating light of the microscope.

To produce appropriately thin tissue sections, it is, possible to freeze the entire tissue sample or embed it in a substrate and harden it to form a solid body. Thin sections may be cut from solid samples relatively easily.

Often, however, thin sections must be produced from soft materials, such as are constituted by most living cell tissues and, in particular, brain tissue. In this case, the cell tissue is mostly located in an aqueous buffer solution. Following the severing of the tissue sample, the tissue section floats to the surface of the buffer solution. Soft materials cannot be sectioned particularly well by standard microtomes, since the material is uncontrollably misshapen during cutting. Therefore, microtomes having a vibrating blade are employed for such materials. In this case, the blade is set to vibrate parallel to the blade cutting edge. The blade cutting edge therefore vibrates transverse to the direction of advancing the cut, a method by which the cutting results are improved.

Vibration microtomes of this type are known from various manufacturers and in two different embodiments. The brochure "Vibratome Sectioning Products" from the firm of Ted Pella Inc., January 1992, 4595 Mountain Lakes; Boulevard, Redding, Calif. 96003, U.S.A., discloses a vibration microtome which uses an electromagnet to excite the oscillation of the blade. In this case, the blade holder is set oscillating by the electromagnet at a constant oscillation frequency which corresponds to the mains frequency of 50 Hz or 60 Hz. As a result of linear guidance of the blade holder, the oscillation of the blade takes place parallel to its cutting edge. The amplitude of the oscillation can be changed to a small extent by adjusting the coil current, in order to adapt somewhat to the sample material.

The brochures "EMS Oscillating Tissue Slicer" from the firm of Electron Microscopy Sciences, 321 Morris Road, Box 251, Fort Washington, Pa. 19034, and "Leica VT 1000 E/M High-Level Quality and Functionality" from the firm of Leica Instruments GmbH, P.O. Box 1120, 96226 Nussloch, Germany, disclose vibration microtomes in which the vibration movement runs parallel to the blade cutting edge, but their drive is carried out by means of an electric motor. The rotational movement of the electric motor is in this case converted into a linear movement via a push rod. Here, the oscillation amplitude remains constant, whereas the oscillation frequency can be adjusted via the rotational speed of the motor. Different oscillation frequencies are beneficial for different sample hardnesses.

DE-B 1 267 873 discloses a microtome having an oscillating blade, in which the oscillation frequency and amplitude are adjustable. For this purpose, two leaf springs are employed, each of which is fastened at one end to the microtome housing, and whose freely oscillating ends are connected to each other via a shaft bearing the microtome blade. The oscillation frequency is set by shortening or lengthening the effective spring length of the leaf springs by means of locking screws. The oscillation amplitude is changed by means of microphone armature structures, which act as electromagnets on the ends of the shaft. As a result of fastening the microtome blade via the shaft to the ends of the leaf springs, the microtome blade moves on a circular arcuate path.

Although the abovementioned vibration microtomes deliver better section results than standard microtomes having fixed blades, they are still not optimal. Furthermore, there is unevenness in the section surface of the sample, for which reason the sample has different layer thicknesses depending on the location. Wave-like layer thickness variations occur most often. Therefore, during an attempt to produce particularly thin sections, it often occurs that the tissue sections fall apart into individual strips, in accordance with the wave-like structures, and therefore become unsuitable for further use or examination. On the other hand, even in the case of cohering tissue, the wave-like thickness differences are disadvantageous and interfere with the examination in the optical microscope, since they bring about differences in brightness which are not founded in the material composition of the sample.

SUMMARY OF THE INVENTION

Accordingly, it would be desirable to improve the section quality of a vibration microtome and, in particular, to achieve a low waviness of the section surface in the case of biological tissue samples.

The present invention provides a microtome comprising a blade oscillating transverse to the direction of advancing a cut, an electric motor having a rotational speed that is controllable, a first eccentric driven by the electric motor, and a connecting element rotatably mounted to the first eccentric by a fastening device at one end, and extending partly through a guide rail and being operatively connected the blade at another end. The fastening device is radially adjustable on the first eccentric by a second eccentric provided on the first eccentric, the second eccentric being rotatable about an axis located outside an axis of rotation of the first eccentric, and the fastening device being articulated on the second eccentric.

The present invention also provides for the fastening device to be radially adjustable on the first eccentric by a displacement device provided on the first eccentric.

BRIEF DESCRIPTION OF THE DRAWINGS

Exemplary embodiments of the invention are explained. in more detail below using the Figures, in which.

DETAILED DESCRIPTION OF THE PREFERRED EMBODIMENT

Figure 1:
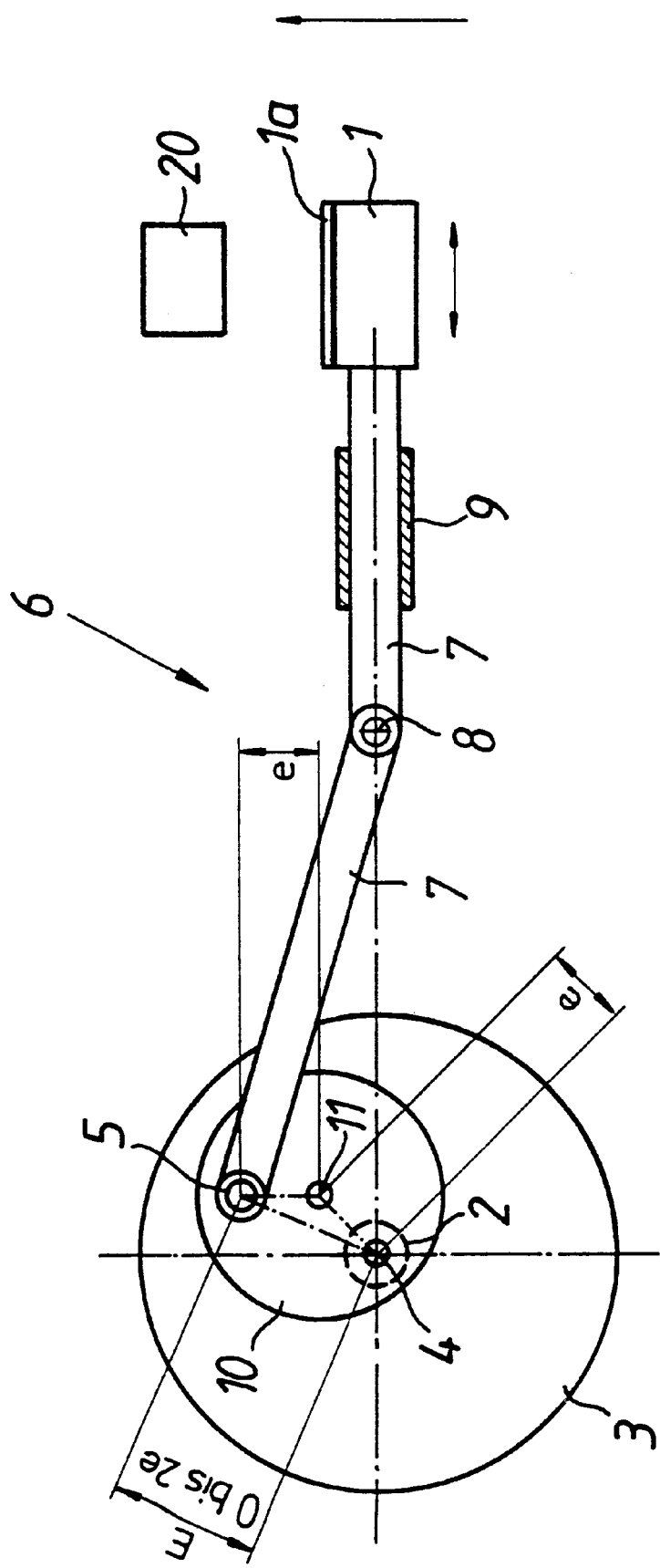
FIG. 1 shows a schematic illustration of the subject of the invention having two eccentrics and a link.

In the Figures, like numerals indicate like parts. FIG. 1 shows a microtome according to the invention having an oscillating blade 1 and having a first eccentric 3 and a second eccentric 10, which are both designed as circular disks. The first eccentric 3 is driven by an electric motor 2, whose axis of rotation in this exemplary embodiment coincides with the axis of rotation 4 of the first eccentric 3. The second eccentric 10 is arranged on the first eccentric 3, and its axis 11 is offset radially by a distance e from the axis of rotation 4. The second eccentric 10 can be rotated with respect to the first eccentric 3 in an adjustable manner about its axis 11. A connecting element 6 is rotatably and eccentrically mounted on this second eccentric 10 by means of a fastening device 5. Part of the connecting element 6 runs in a guide rail 9. The blade 1 is fastened to the end of the connecting element 6. In the exemplary embodiment according to FIG. 1, the connecting element 6 is designed as a link 7 having an articulated connection 8.

As a result of the rotational movement of the first eccentric 3, which is brought about by the electric motor 2, the fastening device 5 of the connecting element 6 runs on a circular line having the eccentric radius E about the axis of rotation 4 of the first eccentric 3. As a result, a linearly directed oscillatory movement of the connecting element 6 in the guide rail 9, and hence an oscillatory movement of the blade 1 parallel to its cutting edge 1a, is generated, as is indicated by a double arrow in FIG. 1. The entire arrangement can be used to cut a tissue sample 20. The blade 1 oscillates transverse to the direction of advancing the cut. It is, of course, possible for the tissue sample 20 to be fed onto the blade 1.

According to the invention, the eccentric radius E can be adjusted by rotating the second eccentric 10 about its axis 11. If in this arrangement the distance between the axis 11 and the fastening device 5 is as large as the distance e between the axis 11 and the axis of rotation 4, then the eccentric radius E can be set arbitrarily between 0 and 2e by rotating the second eccentric 10.

It is thus possible, with the aid of the adjustable eccentric radius E, to set the oscillation amplitude of the blade 1 in a wide range. Since the rotational speed of the electric motor 2 is also controllable, two mutually independent setting parameters for the oscillation of the blade 1 are available. By means of suitable setting of these parameters, as can be demonstrated, the section quality on the tissue sample can be considerably improved. This is mainly expressed by a distinctly reduced waviness of the section surface of the tissue section, with the advantages of a thus enabled thinner tissue section and with the already abovementioned advantages during microscopy.

Figure 2:
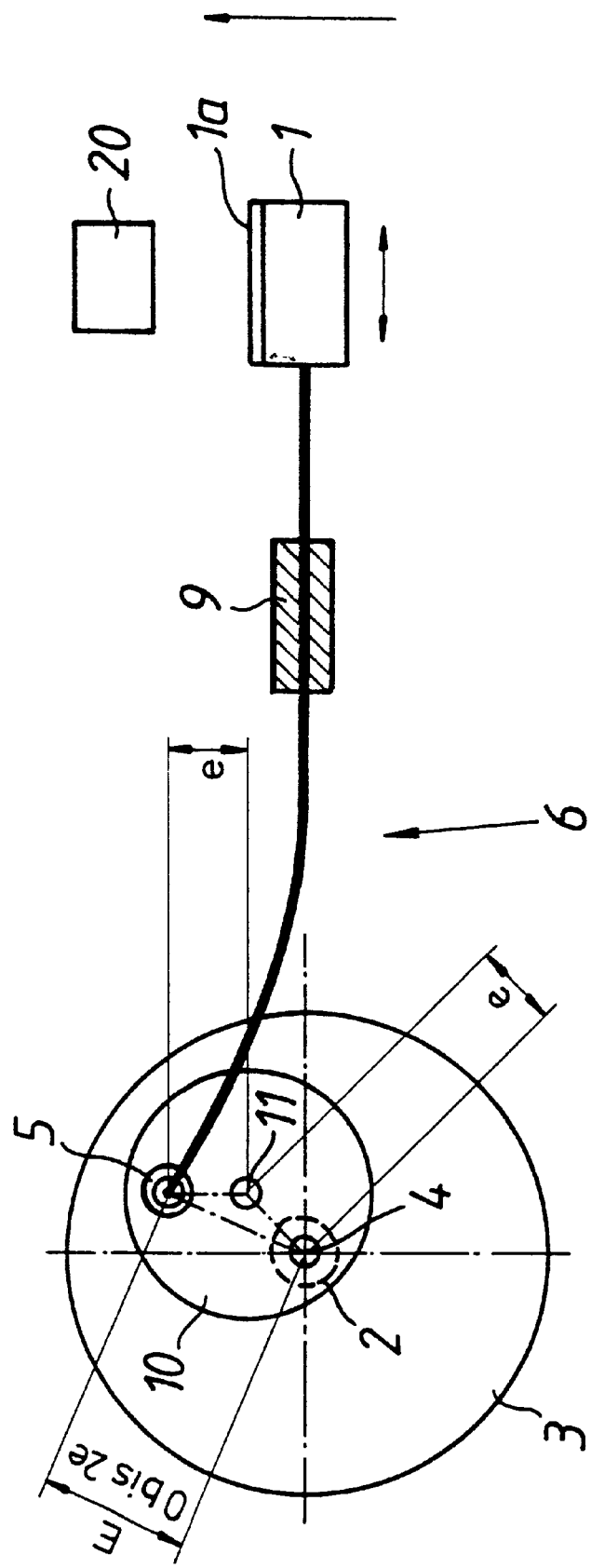
FIG. 2 shows a schematic illustration of the subject of the invention having two eccentrics and a leaf spring.

FIG. 2 shows a similar structure of the invention as FIG. 1, but the connecting element 6 is designed as a leaf spring. On one end, the leaf spring is rotatably mounted on the eccentric 10 by means of the fastening device 5. On the other end, it is partly guided by the guide rail 9, as a result of which it executes a linear movement at this point. The blade 1 fastened thereto thus executes the same linear movement. By means of the leaf spring as connecting element 6, the articulated connection 8 is saved by contrast with the link 7 according to FIG. 1. In addition, the design having a leaf spring shows a more beneficial resonance behavior. In a further embodiment, it is preferable for the part of the leaf spring running in the guide rail 9 to be replaced by a rod, which can then be permanently connected to that part of the leaf spring leading to the fastening device 5.

Figure 3:
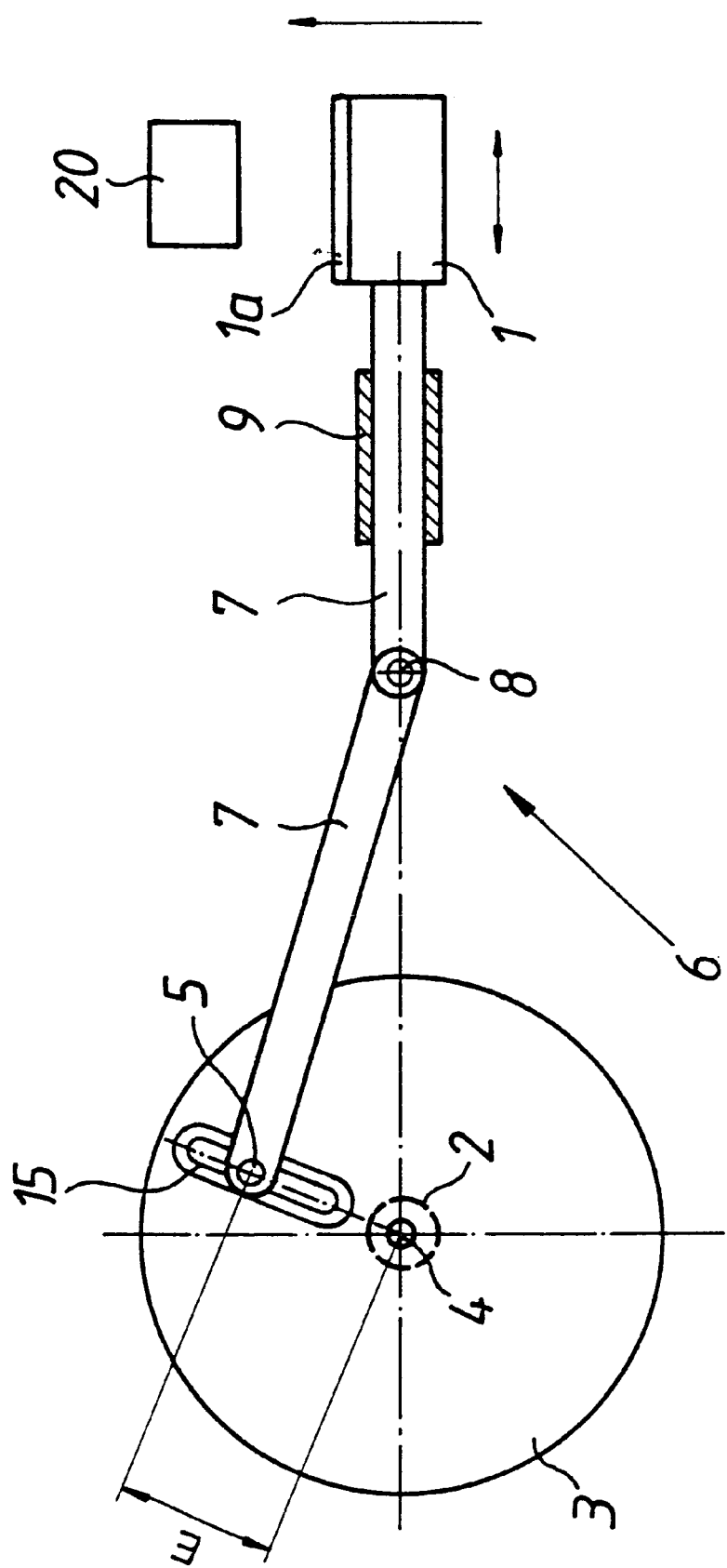
FIG. 3 shows a schematic illustration of the subject of the invention having a displacement device.

A further exemplary embodiment for the adjustment of the oscillation amplitude of the blade 1 is illustrated in FIG. 3. Fitted on the first eccentric 3 is a displacement device 15, with which the fastening device 5 can be displaced radially on the first eccentric 3. The displacement can be performed by means of a setting screw. Alternatively, a clamping mechanism can also be used.

Through many series of examinations, it has transpired that the quality of the section results can be distinctly improved in the case of an oscillating microtome if, at the same time, both a suitable oscillation frequency and an oscillation amplitude matched thereto of the oscillation movement of the microtome blade can be set. Using only a low adjustment of the oscillation amplitude or only an adjustment of the oscillation frequency, it is not possible to achieve particularly good tissue sections.

Through the microtome according to the invention, using the variable setting of oscillation frequency and oscillation amplitude, it is possible for two parameters to be simultaneously altered in wide limits. It has been shown in this case that it is always possible to find a value pair of oscillation frequency and oscillation amplitude for an optimum tissue section for different types and compositions of tissue samples. It is thus possible to a great extent to specifically adapt the microtome to the respective consistency of the tissue sample to be sectioned.

In this case, in particular the waviness of the tissue section is reduced in such a way that, on the one hand, during observation or during measuring of the tissue section in the optical microscope, any remaining residual waviness is no longer visible or perceptible and therefore no longer plays a role. On the other hand, with the reduced waviness of the tissue section, considerably thinner coherent tissue sections are also made possible. Thus, even tissue samples having a relatively high light absorption can be examined in transmitted light. In addition, because of the thinner tissue sections, fewer details of the tissue structure are superimposed, which makes better observation of these details possible.

Other embodiments of the microtome will be apparent to those skilled in the art from consideration of the specification disclosed herein. It is intended that the specification be considered as exemplary only, with the scope and spirit of the invention being indicated by the following claims.

German priority application 196 45 107.8-52, filed Nov. 1, 1996, including the specification, drawings and abstract, is hereby incorporated by reference.

What is claimed is:

1. A microtome apparatus comprising:
   a microtome blade oscillating transverse to the direction of advancing a cut;
   an electric motor having a rotational speed that is controllable;
   a first eccentric driven by the electric motor; and
   a connecting element rotatably mounted to the first eccentric by a fastening device at one end, and extending partly through a guide rail and being operatively connected the blade at another end,
   wherein the fastening device is radially adjustable on the first eccentric by a second eccentric provided on the first eccentric, the second eccentric being rotatable about an axis located outside an axis of rotation of the first eccentric, and the fastening device being articulated on the second eccentric.

2. An apparatus as claimed in claim 1, wherein the first and second eccentrics are circular disks.

3. An apparatus as claimed in claim 1, wherein the connecting element includes a link having an articulated connection.

4. An apparatus as claimed in claim 1, wherein the connecting element includes a leaf spring.

5. An apparatus as claimed in claim 2, wherein the connecting element includes a link having an articulated connection.

6. An apparatus as claimed in claim 2, wherein the connecting element includes a leaf spring.

7. A microtome apparatus comprising:

a microtome blade oscillating transverse to the direction of advancing a cut;

an electric motor having a rotational speed that is controllable;

an eccentric driven by the electric motor; and a connecting element rotatably mounted to the eccentric by a fastening device at one end and extending partly through a guide rail and being operatively connected to the blade at another end, wherein the fastening device is radially adjustable on the eccentric by a displacement device provided on the eccentric.

8. An apparatus as claimed in claim 7, wherein the eccentric is a circular disk.

9. An apparatus as claimed in claim 7, wherein the connecting element includes a leaf spring.

10. An apparatus as claimed in claim 7, wherein the connecting element includes a link having an articulated connection.

* * * * *